United States Patent
Lee et al.

(10) Patent No.: US 6,639,068 B1
(45) Date of Patent: Oct. 28, 2003

(54) METHOD OF PREPARING HIGHLY PURE CEFPODOXIME PROXETIL

(75) Inventors: Gwan-Sun Lee, Seoul (KR);
Young-Kil Chang, Seoul (KR);
Jae-Heon Lee, Yongin-si (KR);
Chul-Hyun Park, Seoul (KR);
Gha-Seung Park, Koyang-si (KR);
Keum-Shin Jung, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 10/111,557

(22) PCT Filed: Nov. 7, 2000

(86) PCT No.: PCT/KR00/01272

§ 371 (c)(1),
(2), (4) Date: Apr. 24, 2002

(87) PCT Pub. No.: WO01/34611

PCT Pub. Date: May 17, 2001

(30) Foreign Application Priority Data

Nov. 8, 1999 (KR) .......................................... 1999-49174

(51) Int. Cl.[7] ............................................. C07D 501/34

(52) U.S. Cl. ..................................................... 540/228
(58) Field of Search ......................................... 540/228

(56) References Cited

U.S. PATENT DOCUMENTS

| | | | | |
|---|---|---|---|---|
| 4,486,425 A | * | 12/1984 | Nakao et al. ................ | 540/230 |
| 5,498,787 A | * | 3/1996 | Wang et al. ................. | 540/222 |
| 5,789,585 A | * | 8/1998 | Lee et al. .................... | 540/450 |

FOREIGN PATENT DOCUMENTS

| EP | 0 620 225 B1 | 3/1994 |
|---|---|---|
| GB | 1598 568 | 4/1978 |

OTHER PUBLICATIONS

The Journal of Antibiotics, vol. 40, Mar. 1987, 370–384, Koichi Fujimoto, et al.

* cited by examiner

*Primary Examiner*—Mark L. Berch
(74) *Attorney, Agent, or Firm*—Anderson Kill & Olick, PC

(57) ABSTRACT

Highly pure cefpodoxime proxetil can be prepared by a simple process comprising the step of reacting a cefpodoxime salt with 1-iodoethylisopropylcarbonate in an organic solvent in the presence of a crown ether.

6 Claims, 5 Drawing Sheets

Retention Time

Retention Time

Retention Time

METHOD OF PREPARING HIGHLY PURE CEFPODOXIME PROXETIL

CROSS REFERENCE TO RELATED APPLICATION

This application is a national stage application filed under 35 U.S.C. 371 of International Application PCT/KR00/01272, with an international filing date of Nov. 7, 2000, now abandoned.

FIELD OF THE INVENTION

The present invention relates to a method of preparing cefpodoxime proxetil of high purity from cefpodoxime.

BACKGROUND OF THE INVENTION

Cefpodoxime proxetil, (R,S)-1-(isopropoxycarbonyloxy)ethyl-(+)-(6R,7R)-7-[2-(2-amino-4-thiazolyl)-2-((Z)-methoxyimino)acetamido]-3-methoxymethyl-8-oxo-5-thia-1-azabicyclo[4,2,0]oct-2-en-2-carboxylate, is a cephalosporin ester pro-drug which, when orally administered, converts to cefpodoxime, an antibacterial agent, through rapid hydrolysis by esterases present on the intestinal wall. Cefpodoxime exhibits a wide range of antibacterial activity against gram positive and negative bacteria, e.g., *Staphylococcus aureus, Streptococcus aureus, E. coli, Klebsiella pneumonia* and *Proteuse vulgaris*, and also a high degree of β-lactamase stability.

The cefpodoxime proxetil of formula (I) is a $\Delta^3$-isomer prepared by various methods.

Hideo Nakao and Koich Huzimoto et al. reported a method of preparing cefpodoxime proxetil by reacting cefpodoxime with iodoalkylcarbonate in the presence of a base such as dicyclohexylamine (see *J. of Antibiotics*, vol. 40, pp. 370 (1987)). But the product obtained by this method is contaminated by about 3 weight % of the $\Delta^2$-isomers of formula (II) formed as a by-product. Due to the structure similarity, it is very difficult to separate the undesired by-product from the $\Delta^3$-isomer. The conversion of the $\Delta^2$-isomer to the $\Delta^3$-isomer has been attempted, but this process requires a series of reactions, and thus is not economically feasible.

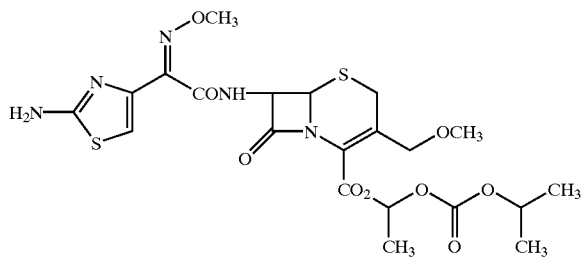

(I)

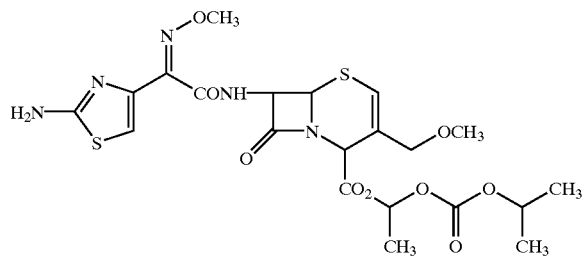

(II)

U.S. Pat. No. 5,498,787 discloses a method of preparing cefpodoxime proxetil from a cefpodoxime salt using a quaternary ammonium salt phase transfer catalyst, e.g., tetrabutylammonium hydrogensulfate in an amount ranging from 35 to 120 mole % based on cefpodoxime. The method can effectively inhibit the formation of the $\Delta^2$-isomer, but has problems in that the yield of the desired products is very low in the range of 50 to 60%, and the use of expensive quaternary ammonium salts is required.

In addition, according to the method disclosed in Korean Publication No. 99-54751, cefpodoxime proxetil is prepared by reacting a cephem compound of cefpodoxime with an alkylcarbonate to obtain an ester and then acylating the ester with an active ester form of arinothiazolyl acetic acid in the presence of a large amount of a quaternary ammonium salt. This method also requires the use of expensive quaternary ammonium salts and suffers from low productivity due to a long process time of about 3 days.

SUMMARY OF THE INVENTION

Accordingly, it is a primary object of the present invention to provide an improved process for preparing cefpodoxime proxetil of high purity.

In accordance with one aspect of the present invention, there is provided a method of preparing cefpodoxime proxetil of formula (I) which comprises reacting a cefpodoxime salt of formula (III) with 1-iodoethylisopropylcarbonate of formula (IV) in an organic solvent in the presence of a crown ether of formula (V):

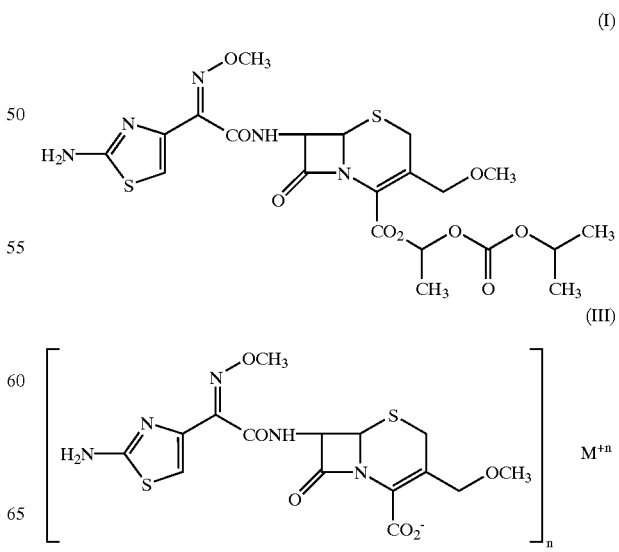

(I)

(III)

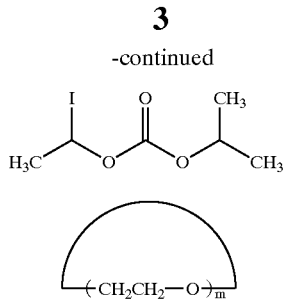

(IV)

(V)

wherein, n is 1 or 2; M is an alkali metal or alkaline earth metal; and m is 4, 5 or 6.

BRIEF DESCRIPTION OF THE DRAWINGS

The above and other objects and features of the present invention will become apparent from the following description of the invention taken in conjunction with the following accompanying drawings, wherein.

DETAILED DESCRIPTION OF THE INVENTION

Figure 1:
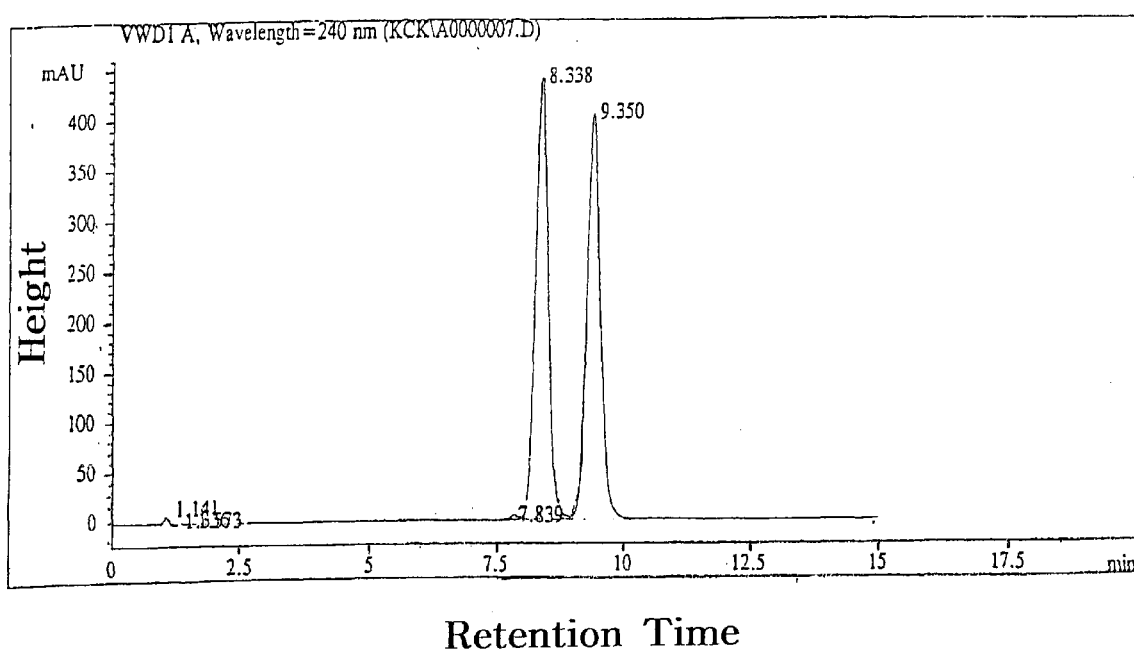
FIGS. 1 to 4 show high performance liquid chromatography (HPLC) scans of cefpodoxime proxetil products obtained by: the method of the present invention (FIG. 1); a method without using a crown ether catalyst (FIG. 2); and conventional methods (FIGS. 3 and 4); respectively, and FIG. 5, that of a commercial product.

The method of the present invention makes it possible to prepare highly pure cefpodoxime proxetil with only a minimal amount of the $\Delta^2$-isomer, by way of reacting a cefpodoxime salt with 1-iodoethylisopiropylcaibonate using a crown ether as a catalyst.

The cefpodoximne salt which is used as the sarting material in the present invention may be a cefpodoxime alkali metal or alkaline earth metal salt, and representative examples thereof include cefpodoxime sodium, potassium, calcium and magnesium salts, or a mixture thereof, among which cefpodoxime sodium salt is preferred.

In accordance with the present invention, 1-iodoethylisopropylcarbonate is employed in an amount ranging from 1 to 3 equivalents, preferably from 1.2 to 1.5 equivalents, based on the amount of the cefpodoxime salt. When 1-iodoethylisopropylcarbonate is added to the cefpodoxime salt slowly or in portions, the formation of the A $^2$-isomer tends to increase, and thus, the addition of 1-iodoethylisopropylcarbonate is carried out in one shot.

The inventive reaction may be performed at a temperature ranging from −10 to 40° C., preferably from 0 to 30° C., for a period ranging from 0.5 to 3.0 hours, preferably from 0.5 to 1.5 hours, in an organic solvent such as acetonitrile, tetrahydrofuran, N,N-dimethylformamide, N,N-dimethylsulfoxide and N,N-dimethylacetamide, preferably in N,N-dimethylacetamide.

Crown ether of formula (V) which is used as a catalyst in the present invention may be referred to as 12-crown-4, 15-crown-5 and 18-crown-6, when m is 4, 5 and 6, respectively. The crown ether catalyst is employed in an amount ranging from 0.5 to 5% by weight based on the weight of the cefpodoxime salt. When the amount of the crown ether catalyst is less than 0.5% by weight, the formation of the $\Delta^2$-isomer increases, while at an amount of more than 5% by weight, the purity of the $\Delta^3$-isomer does not improve significantly. In case the inventive crown ether is not employed, the amount of the $\Delta^2$-isomer formed reaches the range of 6 to 8% by weight.

The method of the present invention is very simple and provides highly pure cefpodoxime proxetil which contains less than 0.5% of the $\Delta^2$-isomer.

The following Examples are given for the purpose of illustration only, and are not intended to limit the scope of the invention.

PREPARATION EXAMPLE 1

Preparation of Cefpodoxime Sodium Salt 2.03 g of sodium 2-ethylhexanoate was dissolved in a mixture of 12.5 ml of N,N-dimethylacetamide and 50 ml of methanol, 5.0 g of cefpodoxime (7-[2-(2-amino-4-thiazolyl)-(Z)-2-(methoxyimino)acetamido]-3-methoxymethyl -3-cephem-4-carboxylic acid) was added thereto, and the mixture was stirred at room temperature for 30 minutes. Then, methanol was removed under a reduced pressure and 50 ml of acetone was added thereto. The solution was stirred for 30 minutes and filtered. The filtered solid was washed with 50 ml of acetone and then with 30 ml of isopropyl ether, and vacuum-dried at room temperature to give 4.98 g of pale yellow cefpodoxime sodium salt (yield: 95%).

$^1$H-NMR($\delta$=, D$_2$O): 3.15(s, 3H, C—OCH$_3$), 3.37(ABq, 2H, C-2), 3.85(s, 3H, =N—OCH$_3$), 4.07(d, 2H, —CH$_2$—OCH$_3$), 5.09(d, 1H, C-6), 5.66(d, 1H, C-7), 6.88(s, 1H, aminothiazole ring-H).

PREPARATION EXAMPLE 2

Preparation of Cefpodoxime Sodium Salt 1.01 g of sodium acetate was dissolved in a mixture of 1 ml of water and 5 ml of methanol, and 5.0 g of cefpodoxime was added thereto, followed by addition of 15 ml of N,N-dimethylacetamide. The mixture was stirred at room temperature for 30 minutes and then, 100 ml of acetone was added thereto. The solution was stirred for 20 minutes and filtered. The filtered solid was washed with 50 ml of acetone and then with 30 ml of isopropyl ether, and vacuum-dried at room temperature to give 5.04 g of pale yellow cefpodoxime sodium salt (yield: 96%).

$^1$H-NMR data obtained was the same as that of Preparation Example 1.

PREPARATION EXAMPLE 3

Preparation of Cefpodoxime Potassium Salt 0.70 g of potassium acetate was dissolved in 5 ml of methanol, and 3.0 g of cefpodoxime was added thereto, followed by addition of 9 ml of N,N-dimethylacetamide. The mixture was stirred at room temperature for 30 minutes and then, 60 ml of acetone was added thereto. The solution was stirred for 20 minutes and filtered. The filtered solid was washed with 50 ml of acetone and then with 30 ml of isopropyl ether, and vacuum-dried at room temperature to give 3.11 g of pale yellow cefpodoxime potassium salt (yield: 95%).

$^1$H-NMR data obtained was the same as that of Preparation Example 1.

PREPARATION EXAMPLE 4

Preparation of Cefpodoxime Magnesium Salt 1.54 g of magnesium acetate tetrahydrate was dissolved in a mixture of 1 ml of water and 3 ml of methanol, and 6.0 g of cefpodoxime was added thereto, followed by addition of 9 ml of N,N-dimethylacetamide. The mixture was stirred at room temperature for 30 minutes and then, 60 ml of acetone was added thereto. The solution was stirred for 20 minutes and filtered. The filtered solid was washed with 100 ml of acetone and then with 60 ml of isopropyl ether, and vacuum-dried at room temperature to give 5.69 g of pale white cefpodoxime magnesium salt (yield: 92%).

$^1$H-NMR data obtained was the same as that of Preparation Example 1.

PREPARATION EXAMPLE 5

Preparation of Cefpodoxime Calcium Salt 1.26 g of calcium acetate monohydrate was dissolved in a mixture of 2 ml of water and 6 ml of methanol, and 6.0 g of cefpodoxime was added thereto, followed by addition of 18 ml of N,N-dimethylacetamide. The mixture was stirred at room temperature for 1 hour and then, 120 ml of acetone was added thereto. The solution was stirred for 20 minutes and filtered. The filtered solid was washed with 100 ml of acetone and then with 60 ml of isopropyl ether, and vacuum-dried at room temperature to give 5.64 g of pale white cefpodoxime calcium salt (yield: 90%).

$^1$H-NMR data obtained was the same as that of Preparation Example 1.

EXAMPLE 1

2.0 g of cefpodoxime sodium salt obtained in Preparation Example 1 or 2 was suspended in 20 ml of N,N-dimethylacetamide, and 0.1 g of 18-crown-6 was added thereto. Then, 1.51 g of 1-iodoethylisopropylcarbonate was added to the suspension in one shot at 20° C. and stirred at room temperature for 30 minutes. 40 ml of ethyl acetate and 40 ml of water were added to the resulting solution, stirred, and the ethyl acetate and aqueous layers were separated. The aqueous layer was extracted with 20 ml of ethyl acetate, the ethyl acetate layers were combined, and washed with a mixture of 30 ml of water and 1 ml of saturated aqueous sodium bicarbonate solution and then with 30 ml of saturated saline. The ethyl acetate solution was treated with activated carbon and anhydrous magnesium sulfate, filtered and concentrated under a reduced pressure to obtain an oily residue. 40 ml of isopropyl ether was added to the residue, stirred for 30 minutes and filtered to obtain 2.13 g of pale yellow cefpodoxime proxetil (yield: 86%).

An HPLC scan of the product is shown in FIG. 1, wherein only a trace amount (0.25%) of the $\Delta^2$-isomer is observed at a retention time of 7.839, while the R- and S-isomers of cefpodoxime proxetil, observed at retention times of 8.338 and 9.350, respectively, constitute 99.0% of the total product.

$^1$H-NMR($\delta$, CDCl$_3$): 1.31(d, 6H, CH(CH$_3$)$_2$), 1.56(d, 3H, CHCH$_3$), 3.30(s, 3H, OCH$_3$), 3.52(br s, 2H, 2-CH$_2$), 4.00(s, 3H, NOCH$_3$), 4.32(s, 2H, 3'-CH$_2$), 4.5~5.2(m, 1H, CH(CH$_3$)$_2$), 5.06(d, 1H, 6-CH), 6.02(dd, 7-CH), 6.72(s, 1H, thiazole ring-H), 6.88 and 6.96(qx2, 1H, CHCH$_3$), 8.06 and 8.10(dx2, whole 1H, 7-NHCO).

EXAMPLE 2

2.0 g of cefpodoxime potassium salt obtained in Preparation Example 3 was suspended in 20 ml of N,N-dimethylacetamide, and 0.06 g of 15-crown-5 was added thereto. Then, 1.44 g of 1-iodoethylisopropylcarbonate was added to the suspension in one shot at 5° C. and stirred at a temperature ranging from 0 to 5° C. for 1.5 hours. 40 ml of ethyl acetate and 40 ml of water were added to the resulting solution, stirred, and the ethyl acetate and aqueous layers were separated. The aqueous layer was extracted with 20 ml of ethyl acetate, the ethyl acetate layers were combined, and washed with a mixture of 30 ml of water and 1 ml of saturated aqueous sodium bicarbonate solution and then with 30 ml of saturated saline. The ethyl acetate solution was treated with activated carbon and anhydrous magnesium sulfate, filtered and concentrated under a reduced pressure to obtain a yellowish red oily residue. 40 ml of isopropyl ether was added to the residue, stirred for 30 minutes, and filtered to obtain 2.02 g of pale yellow cefpodoxime proxetil (yield: 84%).

An HPLC analysis showed that the product contained 0.37% of the $\Delta^2$-isomer and 98.8% of cefpodoxime proxetil (a mixture of R- and S-isomers).

$^1$H-NMR data obtained was the same as that of Example 1.

EXAMPLE 3

3.0 g of cefpodoxime magnesium salt obtained in Preparation Example 4 was suspended in 40 ml of N,N-dimethylacetamide, and 0.1 g of 12-crown-4 was added thereto. Then, 2.65 g of 1-iodoethylisopropylcarbonate was added to the suspension in one shot at room temperature and stirred at 30° C. for 2.5 hours. 60 ml of ethyl acetate and 60 ml of water were added to the resulting solution, stirred, and the ethyl acetate and aqueous layers were separated. The aqueous layer was extracted with 30 ml of ethyl acetate, the ethyl acetate layers were combined, and washed with a mixture of 60 ml of water and 2 ml of saturated aqueous sodium bicarbonate solution and then with 60 ml of saturated saline. The ethyl acetate solution was treated with activated carbon and anhydrous magnesium sulfate, filtered and concentrated under a reduced pressure to obtain a light reddish brown oily residue. 80 ml of isopropyl ether was added to the residue, stirred for 30 minutes, and filtered to obtain 3.12 g of pale yellow cefpodoxime proxetil (yield: 82%).

An HPLC analysis showed that the product contained 0.33% of the $\Delta^2$-isomer and 99.0% of cefpodoxime proxetil (a mixture of R- and S-isomers).

$^1$H-NMR data obtained was the same as that of Example 1.

EXAMPLE 4

3.0 g of cefpodoxime calcium salt obtained in Preparation Example 5 was suspended in 40 ml of N,N-dimethylacetamide, and 0.08 g of 18-crown-6 was added thereto. Then, 2.43 g of 1-iodoethylisopropylcarbonate was added to the suspension in one shot at room temperature and stilled at a temperature ranging from 25 to 30° C. for 2 hours. 60 ml of ethyl acetate and 60 ml of water were added to the resulting solution, stirred, and the ethyl acetate and aqueous layers were separated. The aqueous layer was extracted with 30 ml of ethyl acetate, the ethyl acetate layers were combined, and washed with a mixture of 50 nil of water and 4 ml of saturated aqueous sodium bicarbonate solution and then with 50 ml of saturated saline. The ethyl acetate solution was treated with activated carbon and anhydrous magnesium sulfate, filtered and concentrated under a reduced pressure to obtain a yellowish red oily residue. 80 ml of isopropyl ether was added to the residue, stirred for 30 minutes, and filtered to obtain 3.04 g of pale yellow cefpodoxime proxetil (yield: 81%).

An HPLC analysis showed that the product contained 0.34% of the $\Delta^2$-isomer and 98.9% of cefpodoxime proxetil (a mixture of R- and S-isomers).

$^1$H-NMR data obtained was the same as that of Example 1.

COMPARATIVE EXAMPLE 1

Reaction in the Absence of Crown Ether

The procedure of Example 1 was repeated except that no crown ether was employed, to obtain 2.08 g of pale yellow cefpodoxime proxetil (yield: 83%).

Figure 2:
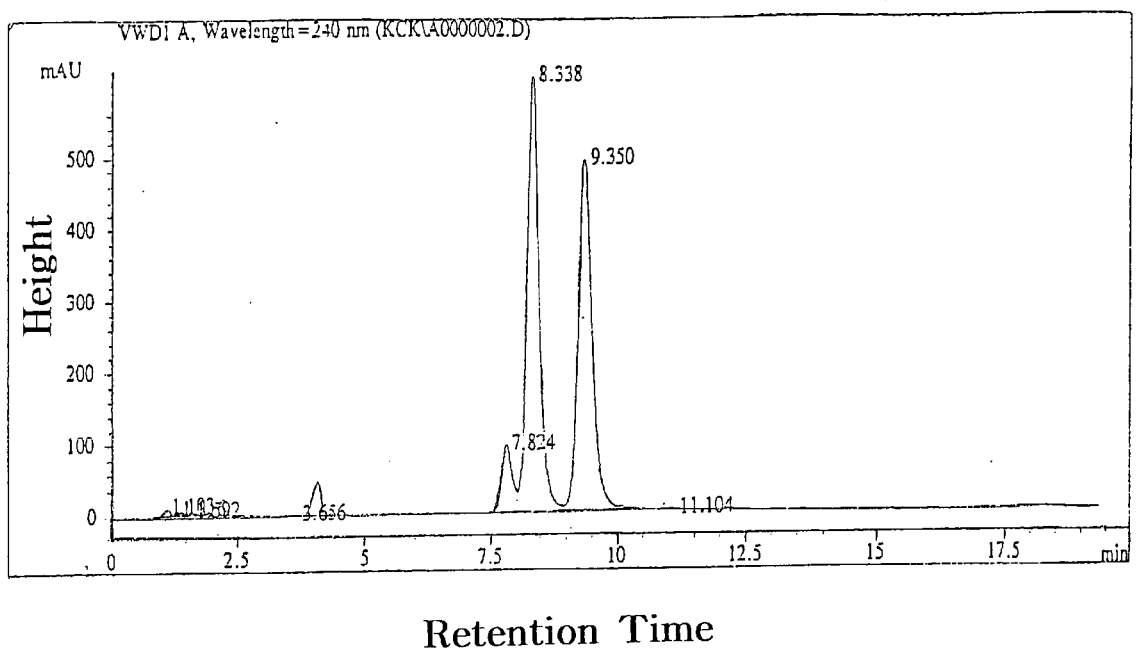

The HPLC scan shown in FIG. 2 suggests that the product contains 7.03% of the $\Delta^2$-isomer (retention time: 7.824) and 91.9% of the $\Delta^3$-isomer (a mixture of the R- and S-isomers at retention times of 8.338 and 9.350, respectively).

$^1$H-NMR data obtained was the same as that of Example 1.

COMPARATIVE EXAMPLE 2

Method of Hideo Nakao and Koich Huzimoto et al.
(*J of Antibiotics* vol. 40, pp. 370 (1987))

2.0 g of cefpodoxime was suspended in 20 ml of N,N-dimethylacetamide and 1.12 ml of dicyclohexylamine was added thereto. Then, 1.82 g of 1-iodoethylisopropylcarbonate was added to the suspension at 20° C. and stirred at room temperature for 2 hours, and the procedure of Example 1 was repeated thereafter to obtain 2.09 g of pale yellow cefpodoxime proxetil (yield: 80%).

Figure 3:
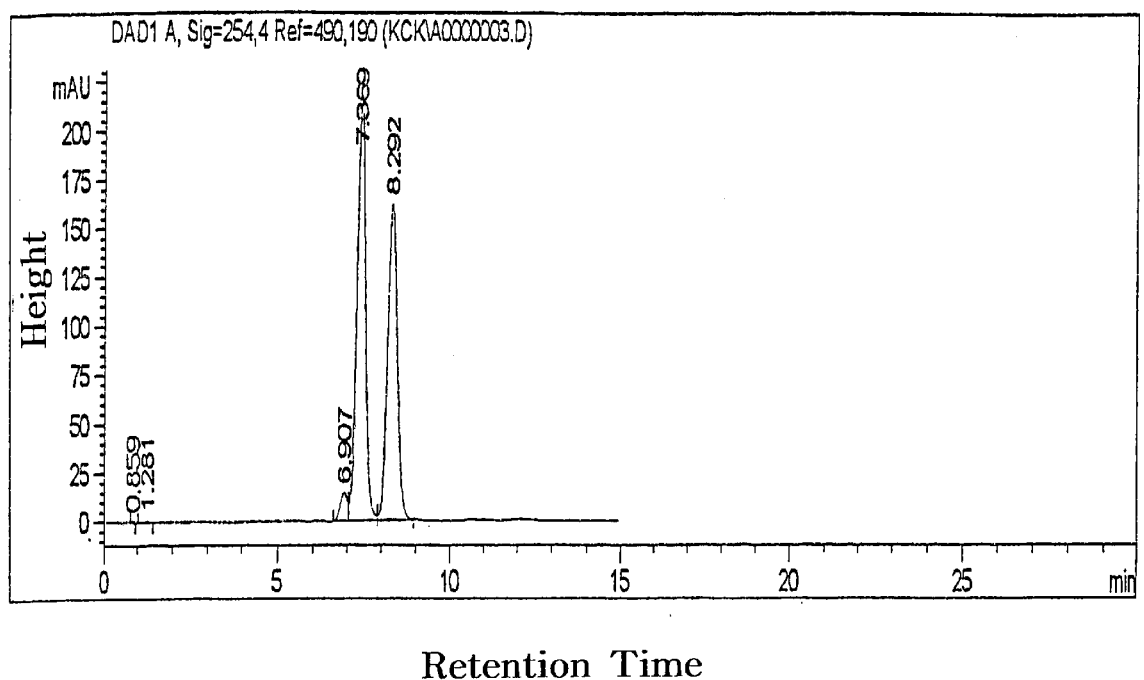

The HPLC scan shown in FIG. 3 suggests that the product contains 3.0% of the $\Delta^2$-isomer (retention time: 6.907) and 96.8% of the $\Delta^2$-isomer (a mixture of the R- and S-isomers at retention times of 7.369 and 8.292, respectively).

$^1$H-NMR data obtained was the same as that of Example 1.

COMPARATIVE EXAMPLE 3

Method Disclosed in U.S. Pat. No. 5,498,787

2.0 g of cefpodoxime sodium salt was suspended in 11 ml of N,N-dimethylacetamide, and 0.6 g of tetrabutylammonium hydrogensulfate and 1.26 g of 1-iodoethylisopropylcarbonate were added thereto at 20° C. The mixture was kept at room temperature, and samples were taken therefrom at reaction times of 1.5 hours, 3 hours and 7 days to be analyzed by HPLC.

Figure 4:
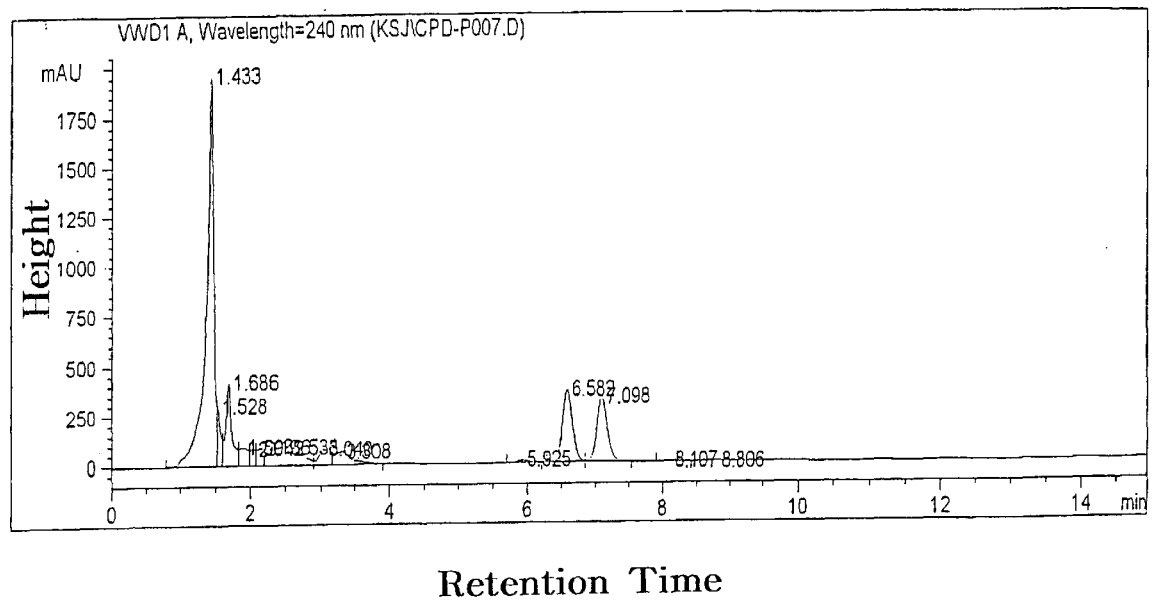

The HPLC scan of the sample taken after 7 days is shown in FIG. 4. An analysis of the result shows the formation of 0.43% of the $\Delta^2$-isomer (retention time: 5.925) together with only 22.6% of the $\Delta3$-isomer (a mixture of R- and S-isomers at retention times of 6.582 and 7.098, respectively).

$^1$H-NMR data obtained was the same as that of Example 1.

REFERENCE EXAMPLE

Figure 5:
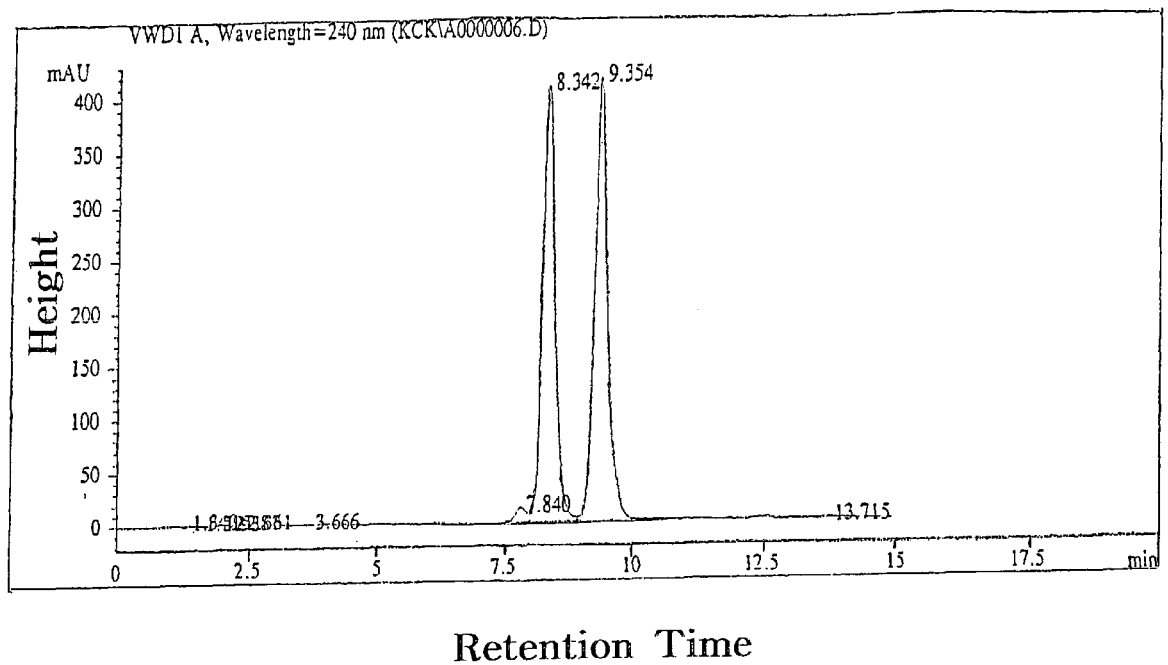

The HPLC scan of a commercial cefpodoxime proxetil sample shown in FIG. 5 suggests that it is composed of 1.44% of the $\Delta^2$-isomer (retention time: 7.840) and 98.1% of the $\Delta^3$-isomer (a mixture of R- and S-isomers at retention times of 8.342 and 9.354, respectively).

As shown above, the method of the present invention is capable of providing highly pure cefpodoxime proxetil in a high yield, as compared with the conventional method.

While the embodiments of the subject invention have been described and illustrated, it is obvious that various changes and modifications can be made therein without departing from the spirit of the present invention which should be limited only by the scope of the appended claims.

What is claimed is:

1. A method of preparing cefpodoxime proxetil of formula (I) which comprises reacting a cefpodoxime salt of formula (III) with 1-iodoethylisopropylcarbonate of formula (IV) in an organic solvent in the presence of a crown ether of formula (V):

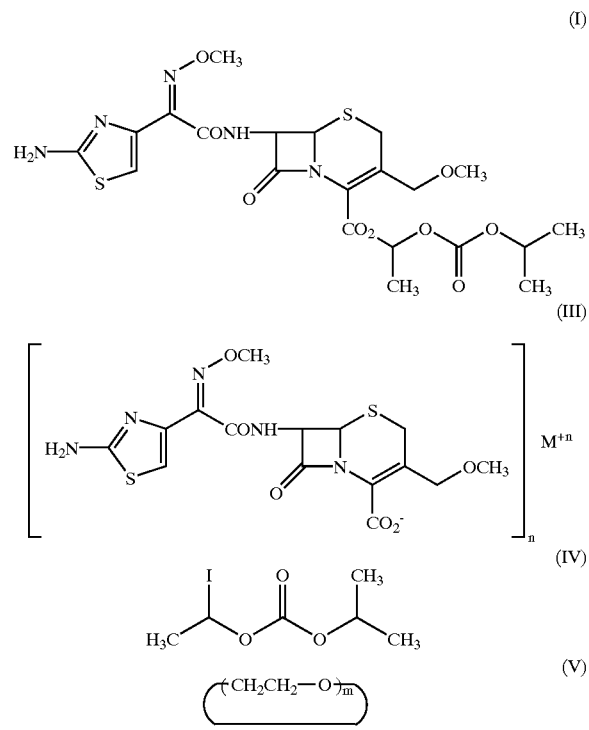

wherein, n is 1 or 2; M is an alkali metal or alkaline earth metal; and m is 4, 5 or 6.

2. The method of claim 1, wherein the cefpodoxime salt is selected from the group consisting of cefpodoxime sodium salt, potassium salt, calcium salt, magnesium salt and a mixture thereof.

3. The method of claim 1, wherein 1-iodoethylisopropylcarbonate is employed in an amount ranging from 1 to 3 equivalents based on the amount of the cefpodoxime salt.

4. The method of claim 1, wherein the reaction is performed at a temperature ranging from −10 to 40° C.

5. The method of claim 1, wherein the crown ether is employed in an amount ranging from 0.5 to 5% by weight based on the weight of the cefpodoxime salt.

6. The method of claim 1, wherein the organic solvent is selected from the group consisting of acetonitrile, tetrahydrofuran, N,N-dimethylformamide, N,N-dimethylsulfoxide, N,N-dimethylacetamide and a mixture thereof.

* * * * *